US006630171B1

United States Patent
Huille et al.

(10) Patent No.: US 6,630,171 B1
(45) Date of Patent: Oct. 7, 2003

(54) PARTICLES BASED ON POLYAMINO-ACID(S) AND METHODS FOR PREPARING SAME

(75) Inventors: Sylvain Huille, Bordeaux (FR); Florence Nicolas, Genas (FR); Nathan Brison, Millery (FR); Gérard Soula, Meyzieu (FR)

(73) Assignee: Flamel Technologies, Venissieux Cedex (FR)

( * ) Notice: Subject to any disclaimer, the term of this patent is extended or adjusted under 35 U.S.C. 154(b) by 0 days.

(21) Appl. No.: 09/856,378

(22) PCT Filed: Nov. 19, 1999

(86) PCT No.: PCT/FR99/02859
§ 371 (c)(1),
(2), (4) Date: Jul. 6, 2001

(87) PCT Pub. No.: WO00/30618
PCT Pub. Date: Jun. 2, 2000

(30) Foreign Application Priority Data

Nov. 20, 1998 (FR) .............................................. 98 14863

(51) Int. Cl.⁷ ................................................. A61K 9/14
(52) U.S. Cl. ...................... 424/489; 424/499; 424/502; 424/484; 424/486; 424/422; 424/130.1; 424/184.1; 514/2; 514/3; 514/56; 514/54
(58) Field of Search ................................ 424/489, 499, 424/502, 484, 486, 422, 130.1, 184.1; 514/2, 3, 56, 54

(56) References Cited

U.S. PATENT DOCUMENTS

| | | | |
|---|---|---|---|
| 4,351,337 A | 9/1982 | Sidman | 128/260 |
| 4,892,733 A * | 1/1990 | Bichon et al. | 424/422 |
| 5,286,495 A | 2/1994 | Batich et al. | 424/490 |
| 5,852,109 A * | 12/1998 | Makino et al. | 524/811 |
| 5,904,936 A | 5/1999 | Huille et al. | 424/489 |
| 6,180,141 B1 | 1/2001 | Lemercier et al. | 424/489 |

FOREIGN PATENT DOCUMENTS

| | | |
|---|---|---|
| WO | 88/01213 | 2/1988 |
| WO | 89/08449 | 9/1989 |
| WO | 91/06286 | 5/1991 |
| WO | 91/06287 | 5/1991 |
| WO | 96/40279 | 12/1996 |
| WO | 97/02810 | 6/1997 |

OTHER PUBLICATIONS

Fox et al. (1977). Molecular Evolution and the Origin of Life: Macromolecules. Dekker Inc, New York.

(List continued on next page.)

*Primary Examiner*—Thurman K. Page
*Assistant Examiner*—Liliana Di Nola-Baron
(74) *Attorney, Agent, or Firm*—James C. Lydon

(57) ABSTRACT

The invention concerns delivery particles (DP's) for active principles (AP's) based on linear amphiphilic polyamino-acids (PAA's), with α-peptide chains, capable of being spontaneously formed by contacting PAA's with a liquid medium, preferably with water, wherein the hydrophile part of the PAA's is solubilized more than the hydrophobic parts of said PAA's, such that the latter precipitate while being organised in discrete supra-molecular arrangements, of average size ranging between 0.01 and 20 µm, capable of combining with at least an AP and releasing the latter in vivo, in prolonged and controlled manner. The inventive suspension is characterised in that the recurrent amino acids (rAA's) constituting the main chain of PAA's are identical to or different from one another and are glutamic acid and/or aspartic acid and/or their salts; and some of said rAA's bear at least one hydrophobic group, said hydrophobic group, being identical to or different from one another. The invention is useful as carriers for active principles, in particular pharmaceutical, insulin or for therapeutic uses.

40 Claims, 1 Drawing Sheet

OTHER PUBLICATIONS

Tsutsumiuchi et al. (1997). Synthesis of Polyoxazoline–(Glyco peptide block copolymers by ring–opening polymerization of (sugar–substituted) alpha–amino acid N–carboxy-anhydrides with polyoxazoline macroinitiators. Macromolecules, 30: 4013–4017.

Akiyoshi et al. (1995). Stabilization of insulin upon macromolecular complexation with hydrophobized polysaccharide nanoparticle. Chenistry Letters, pp. 707–708.

Humphrey, M.J., (1986). Delivery Systems for Peptide Drugs. Davis, Illum, Tomlinson (eds.) Plenum Press, New York, NY.

* cited by examiner

PARTICLES BASED ON POLYAMINO-ACID (S) AND METHODS FOR PREPARING SAME

This application is a 371 of PCT/FR99/02859, filed on Nov. 19, 1999.

The field of the present invention is that of Delivery Particles (DPs) which can be used for the administration of active principles (APs). The latter are preferably medicinal products or nutrients for adminstration to an animal or human organism via the oral, nasal, vaginal, ocular, subcutaneous, intravenous, intramuscular, intradermal, intraperitoneal, intracerebral, parenteral, etc. route. However, they may also be plant-protection products, such as herbicides, pesticides, insecticides, fungicides, etc. In terms of chemical nature, the APs with which the invention is more particularly, but not exclusively, concerned are, for example, proteins, glycoproteins, peptides, polysaccharides, lipopolysaccharides, oligonucleotides and polynucleotides.

The present invention relates more specifically to Delivery Particles, advantageously of the submicron type, based on polyamino acids (PAAs). The present invention is directed toward both naked particles per se, and AP vector systems consisting of particles loaded with the AP(s) under consideration. The present invention also relates to aqueous colloidal suspensions comprising these DPs.

The invention also relates to processes for preparing said particles and colloidal suspensions, with and without APs.

The aim of the encapsulation of APs in DPs is in particular to increase the bioavailability of said APs. Many encapsulation techniques have already been proposed. Such techniques are directed, firstly, toward enabling the AP to be transported to its site of therapeutic action, while at the same time protecting it against the body's attacks (hydrolysis, enzymatic digestion, etc.) and, secondly, toward controlling the release of the AP over its site of action, in order to maintain the amount available to the organism at the desired level. The APs with which these misadventures of delivery and residence in the body are concerned are, for example, proteins, but may also be any other products, of synthetic or natural origin. The review by M. J. HUMPHREY (Delivery System for peptide Drugs, edited by S. DAVIS and L. ILLUM, Plenum Press, N.Y., 1986), gives an account of the problem concerning the improvement of the bioavailability of APs and the advantage of systems for delivery and controlled release.

Of all the materials which can be envisaged for making up DPs, polymers are increasingly used on account of their intrinsic properties. As regards the list of specifications which it is desired to obtain for such DPs, this is particularly demanding and comprises, in particular, the following specifications.

1—It should advantageously be possible to obtain a particle size distribution which is controlled and suitable for the mode of administration chosen and/or for the therapeutic site targeted.
2—It is desirable for the DPs to protect the AP until the site of release is reached.
3—The DPs should advantageously control the rate of release of the AP.
4—It is preferable for the polymer which constitutes the DPs to be biocompatible, able to be eliminated (by excretion) and/or biodegradable and, better still, for it to be metabolized into products which are nontoxic to the body.
5—It is also advantageous for the polymer which constitutes the DPs not to induce an immune response.
6—Finally, it is also desirable for it to be possible to obtain the DPs and the DP-AP systems using a process which does not denature the AP.

The prior technical propositions, described above, have attempted to satisfy this set of specifications. By way of illustration, mention will be made of prior propositions (a) to (h): according to a first approach, which comprises propositions (a) to (d), the inclusion of the active principle takes place during the formation of the delivery supports; according to a second approach, mentioned in propositions (e) to (h), DPs are produced which are capable, once manufactured, of associating spontaneously by absorption to the AP.

(a) Patent U.S. Pat. No. 5,286,495 relates to a process of encapsulation by spraying proteins in aqueous phase, using materials having opposite charges, namely: alginate (negatively charged) and polylysine (positively charged). This manufacturing process makes it possible to produce particles greater than 35 $\mu$m in size.

(b) In addition, emulsion techniques are commonly used for preparing microparticles loaded with AP. For example, patent applications WO 91/06286, WO 91/06287 and WO 89/08449 disclose such emulsion techniques in which use is made of organic solvents in order to solubilize polymers, for example of the polylactic type. However, the solvents have proven to be possibly denaturing, in particular for peptide or polypeptide APs.

(c) Biocompatible DPs formed in aqueous solution and called proteinoids, described as early as 1970 by W. FOX and K. DOSE in "Molecular Evolution and the origin of Life", Ed. Marcel DEKKER Inc. (1977), are also known. Thus, patent application WO 88/01213 provides a system based on a mixture of artificial polypeptides obtained by thermal condensation of amino acids. The microparticles according to that invention are obtained by changing the pH, which causes precipitation of the proteinoid particles.

(d) Mention will also be made, as a matter of interest, of U.S. Pat. Nos. 4,351,337 and 4,450,150. which are the product of a field other than that of the delivery of APs, characteristic of the invention. These patents disclose implants of masses attached and located at quite precise sites in the body. The implants are produced from polymeric materials of the poly-$\alpha$-amino acid type (Leu/GluOH and GluOEt/GluOH, respectively). According to the teaching of that patent, the preferred polyamino acids are those which are rich in hydrophobic amino acid (eg. more than 50% of Leucine or of Glu OEt) and water-insoluble. The AP can be incorporated into a solution of poly-$\alpha$-amino acid in an organic solvent. This solution is that used to form the implant by molding/drying (evaporation). According to another variant, the AP can be included in the core of a microcapsule, the case of which is obtained using a copolymer solution, and the diameter of which is greater than or equal to 5000 $\mu$m. The core can consist of pure AP or of a copolymer matrix which includes the AP, and can be obtained from the solution of PAA in an organic solvent.

(e) PCT patent application WO/FR97/02810 discloses a composition for the controlled release of active principles, comprising a plurality of lamellar particles of a biodegradable polymer, at least partly crystalline (lactic acid polymer), and of an active principle absorbed onto said particles. The release of the active principle takes place by desorption.

(f) The publication "*CHEMISTRY LETTERS* 1995, 707, AKIYOSHI et al" relates to the stabilization of insulin by supramolecular complexation with nanoparticles formed from ten or so polysaccharide chains made hydrophobic by grafting cholesterol.

(g) The article published in "*MACROMOLECULES* 1997, 30, 4013–4017" describes copolymers composed of a peptide block based on L-phenylalanine, on γ-benzyl-L-glutamate or on O-(tetra-O-acetyl-β-D-glucopyranosyl)-L-serine, and a synthetic block, such as poly(2-methyl-2-oxazoline) or poly(2-phenyl-2-oxazoline). Some of these polymers aggregate in aqueous medium to form particles of 400 nm, capable of associating with an enzyme, lipase.

(h) The subject of patent FR 95-03978 is polyamino acid particles which can be used for delivering active principles and which are characterized in that their constituent polyamino acids comprise at least two types of recurrent amino acids, AANs (which are neutral and hydrophobic) and AAIs (which are ionizable and hydrophilic). The particles are obtained spontaneously by dispersion of the polyamino acid powder in an aqueous solution. The particles thus obtained associate spontaneously in aqueous suspension with active principles, which are for example protein in nature.

These prior technical propositions more or less satisfy the specifications of the list of specifications indicated above. However, such delivery particles for active principles remain perfectible.

Given this irrefutable fact, one of the essential objectives of the present invention is to improve the prior technical proposition referenced (h) FR 95-03 978, by providing novel DPs based on linear, amphiphilic poly-α-amino acids (PAAs), the hydrophilic and hydrophobic natures of which are, respectively, provided by the amino acids of the main chain of the polymer and by hydrophobic radicals attached laterally to a fraction of the amino acids via a covalent attachment. This improvement concerns more precisely a means of controlling the characteristics of the association between the APs and DPs in order to improve the degree of loading of AP, and/or to improve the kinetics of release of the AP.

Another essential objective of the invention is to provide an aqueous colloidal suspension of delivery particles for active principles, which comprises PAA particles which satisfy the specifications targeted above and which constitutes a pharmaceutical form which is appropriate and suitable for administration, for example oral administration, to humans or animals.

Another essential objective of the invention is to provide a process for preparing PAA particles which can be used in particular as vectors of active principles, said process having to be even more economical, simpler to carry out and nondenaturing for the active principles, and also still having to allow fine control of the mean particle size of the particles obtained.

Another essential objective of the invention is the use of the abovementioned suspensions and particles for preparing medicinal products (e.g. vaccines) and/or nutrients, in particular for administration, especially oral, nasal, vaginal, ocular, subcutaneous, intravenous, intramuscular, intradermal, intraperitoneal, intracerebral or parenteral administration, of active principles such as proteins, glycoproteins, peptides, polysaccharides, lipopolysaccharides, oligonucleotides or polynucleotides.

Another essential objective of the present invention is to provide suspensions of DPs which are partly submicron and micron particles, which are based on PAA and which can be used as vectors for an AP, in particular medicinal and/or nutrient APs, for the administration of said AP to a human or animal organism.

Another objective of the present invention is to provide a medicinal product, such as a system for sustained release of active principles, which is easy and economical to produce and which is also biocompatible and capable of ensuring a very high level of bioavailability of the AP.

Another essential objective of the invention is to provide a system for delivering vaccine, which is nonimmunogenic intrinsically and in combination with one or more antigens.

The objectives relating to the products, inter alia, are achieved through the present invention which relates, first of all, to particles which can be used in particular for the delivery (DPs) of active principle(s), which are of the type of those:

based on amphiphilic, linear polyamino acids (PAAs) with α-peptide chains;

capable of forming spontaneously by bringing the PAAs into contact with a liquid medium, preferably with water, in which the hydrophilic portion of the PAAs solubilizes more than the hydrophobic portion of said PAAs, such that the latter precipitate while becoming organized in discrete supramolecular arrangements;

having a mean size of less than 200 μm, preferably less than 100 μm, and even more preferably of between 0.01 and 20 μm;

and capable of associating with at least one AP and of releasing the latter in vivo, in a sustained and controlled way;

characterized:

in that the recurrent amino acids (rAAs) constituting the main chain of the PAAs are identical to or different from one another, and are chosen from amino acids of acid type, and preferably from the group comprising glutamic acid and/or aspartic acid and/or the salts thereof, respectively glutamates and aspartates, and in that some of these rAAs each bear at least one hydrophobic $R^0$ group, these hydrophobic $R^0$ groups being identical to or different from one another.

One of the conditions for the particles according to the invention to form is that the hydrophilic portion of the PAAs solubilizes more in the liquid suspension medium than the hydrophobic portion thereof.

The recurrent amino acids (rAAs) selected in accordance with the invention are amino acids containing carboxylic functions (Glu and Asp) in COOH form or in the form of salts (carboxylates) $COO^-$, $X^+$; with X corresponding to alkali metals, preferably to Na.

It is to the applicant's credit to have chosen, by way of material constituting the DPs, a particular class of poly-α-amino acids, the (co)monomers of which are recurrent amino acids (rAAs) of polar nature, and which have been made amphiphilic by modifying the hydrophilic nature by adding hydrophobic side chains to a fraction of the rAAs. This acquired amphiphilic nature confers on the PAAs the possibility of forming colloidal suspensions of DPs, compatible with the pH of the physiological media encountered in the applications intended.

This selection advantageously makes it possible to have a greater choice regarding the nature of the hydrophobic groups, and thus a better means of controlling the hydrophobicity of the polymer and of the DP, thereby making it possible to optimize the association and the release of the APs.

The structure of the PAA polymer, the nature of the amino acids Asp and Glu and the hydrophobic radicals are chosen such that the polymer chains spontaneously become structured in the form of particles which are small in size and stable in physiological medium.

The structure of the PAA polymer, the nature of the amino acids Asp and Glu and the hydrophobic radicals are chosen such that the DPs encapsulate proteins, or other APs, in aqueous medium via a mechanism which is spontaneous and nondenaturing for proteins.

The structure of the PAA polymer, the nature of the amino acids Asp and Glu and the hydrophobic radicals are chosen such that the DPs release the APs into physiological medium and, more precisely, in vivo, the kinetics of release depending on the nature of the polymer and of the DPs which it is capable of forming.

Without it being limiting, this selection is directed, more specifically, toward PAAs, the main chain of which consists of rAAs which are identical to one another. The primary structure of the PAAs can be of the ordered, alternating block type (block PAAs) or of the disordered, random block type (random PAAs) According to a preferred characteristic of the invention, the PAAs are polymers containing up to approximately 1000 rAAs, and preferably up to approximately 500 rAAs, and even more preferably up to approximately 200 rAAs.

The hydrophobic $R^0$ groups participate in the aggregation of the polymeric chains, which is at the heart of the formation of the DPs. According to a preferred arrangement of the invention, these $R^0$ groups are identical to or different from one another, and selected from the group comprising:

(i) linear or branched, preferably linear, $C-C_{20}$, and even more preferably $C_2-C_{18}$, alkyls, acyls or alkenyls;

(ii) hydrocarbon-based groups containing one or more heteroatoms, preferably those containing oxygen and/or sulfur, and even more preferably those of the following formula:

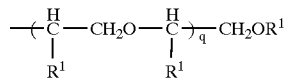

in which:
the $R^1$ radicals are identical to or different from one another, and correspond to hydrogen or to a radical satisfying the same definition as that given above in point (i),
q=1 to 100;

(iii) aryls, aralkyls or alkylaryls, preferably aryls;

(iv) natural hydrophobic derivatives, preferably cholesterol, phosphatidylcholines and diacylglycerols.

For the purpose of the present invention, the term "hydrocarbon-based groups" is intended to mean groups comprising in particular hydrogen and carbon atoms.

Preferably, the $R^0$ groups are selected from the following group of radicals: methyl, ethyl, propyl, dodecyl, hexadecyl, octadecyl.

In accordance with the invention, each hydrophobic $R^0$ group is attached to the main chain via a covalent attachment which can be cleaved, preferably by chemical and/or enzymatic hydrolysis, said attachment being more especially of the ester or amide type.

Advantageously, the fraction of rAA monomers bearing hydrophobic groups represents a proportion greater than or equal to 3%, preferably between 3–70%, and even more preferably between 13 and 60%.

In practice, the PAAs constituting the DPs of the suspension according to the invention are, for example:
polymers based on glutamate:
poly(sodium glutamate)-block-(methyl glutamate),
poly(sodium glutamate)-block-(ethyl glutamate),
poly(sodium glutamate)-block-(propyl glutamate),
poly(sodium glutamate)-block-(octadecyl glutamate),
poly(sodium glutamate)-block-(benzyl glutamate),
poly(sodium glutamate)-co-(methyl glutamate),
poly(sodium glutamate)-co-(ethyl glutamate),
poly(sodium glutamate)-co-(propyl glutamate),
poly(sodium glutamate)-co-(dodecyl glutamate),
poly(sodium glutamate)-block-(octadecyl glutamate),
polymers based on aspartate:
poly(sodium aspartate)-block-(methyl aspartate),
poly(sodium aspartate)-block-(ethyl aspartate),
poly(sodium aspartate)-block-(propyl aspartate),
poly(sodium aspartate)-block-(octadecyl aspartate),
poly(sodium aspartate)-block-(benzyl aspartate).

Advantageously, the DP particles have a mean size of between 0.01 μm and 0.5 μm, preferably between 0.01 and 0.2 μm. For the purpose of the invention, the term "mean size" or "mean particle size" is intended to mean the arithmetic mean of the diameters by volume [D4,3], established by laser scattering, and the diameter of gyration measured by elastic light scattering.

One of the assets of the invention is that it has achieved very good control of the mean particle size of these matricial entities and of their particle size distribution. This control involves attaining particle sizes which are extremely small, of the order of a few nanometers, and of very low polydispersity, in the knowledge that it is possible to increase the size of these nanoparticles by aggregation.

The control of the DP size takes place via the composition of rAA and $R^0$ of the polyamino acids, but also, for the same composition, through the choice of a block structure and of the production process.

According to an alternative regarding the size of the DPs of the suspension according to the invention, said delivery particles DP are aggregated in order to obtain new particles which are bigger in size.

The PAA material constituting the DPs according to the invention is preferably a homopolymer or a copolymer in which the rAA=Asp and/or Glu, and which has been made amphiphilic by modifying the hydrophilic nature of this rAA by adding hydrophobic $R^0$ side chains to a fraction of the rAAs. This acquired amphiphilic to a fraction of the rAAs. This acquired amphiphilic nature makes it possible to bring together at least three novel and surprising properties:

1. the first is the possibility of spontaneously forming colloidal suspensions of DPs compatible with the pH of the physiological media encountered in the therapeutic applications intended;

2. the second is the spontaneous association of the DPs with Ads in the absence of an agent other than water, water being used as solvent of the DPs, and water being not denaturing for the APs in the case where APs are proteins;

3. the third is the possibility of releasing the AP of the AP-DP association complex, under physiological conditions, with pharmacokinetic and pharmacodynamic profiles which allow uses in the therapeutic domain to be envisaged.

The APs, in particular the APs which are protein in nature, are in fact trapped by the delivery particles DP, which can be compared to matrices made of water and of PAAs in which the AP(s) are dispersed. Their release takes place either by spontaneous dissociation, or in the course of the degradation of the PAAs and of the subsequent destructuring of the particles. The trapping of the Ads is produced spontaneously by simply mixing them in an aqueous colloidal suspension of DPs according to the invention.

The particles DP loaded with at least one active principle AP constitute another subject of the present invention.

According to another of its aspects, upstream of the particles, which form its essential subject, the invention also relates to the precursors of the DPs, which precursors are the PAAs selected, as defined above.

Downstream of the DPs, the invention also encompasses the colloidal, preferably aqueous, suspension of particles as defined above. controlled release, of said DP in vivo, for therapeutic purposes.

The invention relates, moreover, to a process for preparing the abovementioned colloidal suspension of particles, e.g. of delivery particles (DPs) for active principles (APs), characterized in that it consists, essentially:

I—in using linear PAAs containing α-peptide chains of recurrent amino acids (rAAs) selected from natural polar amino acids, namely glutamic acid and aspartic acid, and/or from the salts thereof, respectively glutamates and aspartates; some of these rAAs each bearing at least one hydrophobic $R^0$ group, these $R^0$ groups being identical to or different from one another;

II—in placing the amphiphilic PAAs in a solvent, preferably aqueous, medium;

III and then in making at least the rAAs carrying $R^0$ insoluble in the medium, so as to precipitate these rAAs and thus to form discrete supramolecular arrangements.

According to an advantageous variant of this process, at least one active principle is incorporated into the liquid medium containing the particles DP, so as to obtain a colloidal suspension of DPs loaded with active principle(s).

In addition, in order to increase the size of the particles, it is conceivable to anticipate, in this process for preparing the suspension, at least one additional step of aggregation of the particles, using at least one aggregation agent consisting of a salt and/or an acid and/or a base and/or a polymer, optionally an ionic polymer (eg. polylysine, polyethyleneimine, etc.). For greater detail, reference will be made to patent application FR 95-03 918.

After having gone through the essential characteristics of the invention in terms of particles, of PAA precursors of said particles, of a colloidal suspension of these particles and of preparation of this suspension, it is now appropriate to develop a little further, firstly, the aspect of production of the PAAs and of the particles which may or may not be loaded with AP and, secondly, the aspect of use of the DPs and of the suspensions of these DPs in medicinal systems for sustained and controlled release of AP.

The PAAs are obtained in a way known in itself. In this respect, reference will be made, for example, to: *"Encyclopedia of Polymer Science and Engineering*, volume 12, p. 786; John Wiley & Sons". In the context of the invention, use is preferably made of polymerization techniques which involve N-carboxy-α-amino acid anhydrides, the preparation of which is given, for example, in: *"Biopolymers*, 15, 1869 (1976)". Regarding the techniques for polymerizing these N-carboxy-α-amino acid (NCA) monomers, details are given in the book by H. R. KRICHELDORF "α-*Aminoacid-N-Carboxy Anhydride and Related Heterocycles" Springer Verlag* (1987).

The nature of the distribution of the hydrophobic groups on the polymer chains is random or ordered, depending on the synthetic pathway chosen. In this respect, there is a multitude of reaction schemes which produce the PAAs selected as raw material for the production of the DPs according to the invention. The three reaction schemes are given hereinafter in a nonlimiting capacity:

(i) synthesis or use (step A) of a PAA copolymer comprising at least two types of hydrophobic recurrent groups, $R^{01}$ and $R^{02}$, and then, by selective elimination (step B), at least one of them is eliminated so as to regenerate rAA in its unmodified state (for example, $R^{01}$=methyl; $R^{02}$=benzyl; step B is a step of debenzylation by hydrogenation, by addition of HBr, etc.);

(ii) synthesis or use (step A) of a hydrophobic PAA homopolymer comprising (exclusively) hydrophobic recurrent amino acids ($R^0$-rAAs) which all bear the same hydrophobic $R^0$ group (eg. methyl, ethyl, propyl, benzyl, stearyl), and then the partial elimination (step B) of part of the $R^0$ groups (eg. by virtue of hydrolysis or saponification of the poly(methyl glutamate) PAA);

(iii) synthesis or use (step A) of a hydrophilic PAA homopolymer comprising (exclusively) hydrophilic recurrent amino acids, rAAs, and then partial hydrophobization (step B) by formation of a covalent attachment with one or more $R^0$ groups (eg. by esterification using fatty alcohols or by ionic displacement using an alkyl halide).

In these three variants (i), (ii) and (iii) the linking unit for grafting the hydrophobic $R^0$ groups onto the pendent side chain of the rAAs is advantageously an ester or amide function.

In practice, the hydrophobic PAA copolymers used in variant (i) are, for example, copolymers of glutamic acid and/or of aspartic acid, in which the pendent carboxylic side functions are protected by esterification according to techniques known to those skilled in the art. They may be, for example, copoly(stearyl glutamate-benzyl glutamate) obtained by polymerization of $rAA_{01}$ (Glu-O-stearyl) N-carboxyanhydride and $rAA_{02}$ (Glu-O-benzyl) N-carboxyanhydride.

The partial hydrophilization of the co-PAA results from the selective elimination of one of the $R^0$ groups, by hydrolysis and/or saponification. This is equivalent to a deprotection which, in the example above, is selective debenzylation. The differences in sensitivity to cleavage of the various esters making up the hydrophobic groups $R^{01}$ and $R^{02}$ are exploited herein. By way of examples of known deprotection processes, mention may be made of those by saponification of methyl esters (STAHMAN et al.; J. Biol. Chem., 197, 771 (1952); KYOWA HAKKO, FR 2 152 582) or by debenzylation [BLOUT et al.; J. Amer. Chem. Soc., 80, 4631 (1958)].

With regard to variant (ii), the hydrophobic PAA homopolymer is, for example, poly(stearyl glutamate) obtained by polymerization of Glu-O-stearyl NCA. The partial hydrolysis of this hydrophobic homopolymer according to the abovementioned known deprotection methods produces a poly(glutamate)-co-(stearyl glutamate).

In variant (iii), the hydrophilic PAA homopolymer can, for example, be polyglutamic acid or a polyglutamate, synthesized by polymerization of glutamic acid NCA. The hydrophobization of this type of poly Glu PAA is carried out, for example, by reaction with stearyl iodide in basic medium. This produces poly(glutamate)-co-(stearyl glutamate). This type of technique is in particular described in [Polymer Bulletin, 32, 127 (1994)].

The formation of the DPs in liquid medium, in the form of a colloidal suspension in accordance with the invention, can be carried out during or after the synthesis of the amphiphilic PAAs defined above.

According to a preference of the invention, the formation of particles takes place by the addition of water or of salt to a solution of PAA, carrying R0 groups, dissolved in a solvent. This operation preferably consists in decreasing the solubility of the hydrophobic fraction so that it precipitates and, in so doing, causes the formation of the particles. Those skilled in the art are capable of finding other simple means for decreasing the solubility of the hydrophobic portion of the polymer, for example by modifying the temperature or the solvent(s), or by combining different techniques.

The preparation of the colloidal suspension of DPs is advantageously followed by a purification step involving techniques known to those skilled in the art, such as distillation, filtration, modification of the pH, chromatography and/or dialysis. Such methods make it possible to eliminate the unwanted salts or solvents. After this optional purification step, a colloidal suspension of DPs is obtained, which can be used directly or which can conceivably be isolated or recovered, in the context of a step IV, by any physical means which is known in itself and suitable, such as for example by filtration, by ultrafiltration, by density gradient separation, by centrifugation, by precipitation, optionally by adding salt, or by lyophilization.

According to a variant of the invention, the process for preparing the colloidal suspension is characterized in that at least one active principle is incorporated into the liquid medium containing the particles DP, so as to obtain a colloidal suspension of DPs loaded or associated with one or more active principle(s) AP.

This incorporation, which produces trapping of AP by the DPs, can be carried out in the following way:

dissolving AP in aqueous solution, and then adding the DPs, either in the form of a colloidal suspension or in the form of isolated DPs (lyophilizate or precipitate);

or adding AP, either in solution or in the pure or preformulated state, to a colloidal suspension of particles DP, optionally prepared extemporaneously by dispersing dry DPs in a suitable solvent, such as water.

The active principle, which is capable of being associated with the particles according to the invention, can be medicinal and/or nutritional. It is preferably chosen from:

proteins and/or peptides, among which the most preferably selected are: hemoglobins, cytochromes, albumins, interferons, antigens, antibodies, erythropoietin, insulin, growth hormones, factor IX, interleukins, or mixtures thereof, polysaccharides, heparin being more particularly selected, nucleic acids, and preferably oligonucleotides of RNA and/or of DNA, vitamins, amino acids and trace elements, and mixtures thereof.

The present invention is also directed toward the precursors of these particles DP consisting of the specific PAAs defined above and characterized in that they contain medicinal APs of the type of those listed above, in particular insulin, and/or APs formed by at least one vaccine, or nutritional, plant-protection or cosmetic APs.

The present invention also relates to the colloidal suspensions of DPs, characterized in that they contain the same APs as those set out above, in particular for the DP precursors.

Finally, the present invention relates to the medicinal products, or the pharmaceutical or nutritional specialties, comprising the DPs loaded with AP and defined above.

According to another of its aspects, the invention is also directed toward the use of these DPs loaded with AP, for manufacturing medicinal products such as systems for controlled release of AP.

In the case of medicinal products, they may, for example, be those which can preferably be administered orally, nasally, vaginally, ocularly, subcutaneously, intravenously, intramuscularly, intradermally, intraperitoneally, intracerebrally or parenterally.

The cosmetic applications which can be envisaged are, for example, compositions which can be applied via transdermal routes.

The plant-protection products concerned may, for example, be herbicides, pesticides, insecticides, fungicides, etc.

A subject of the present invention is also the plant-protection and cosmetic compositions comprising DPs loaded with APs of the type of those targeted above.

The examples which follow will make it possible to more clearly understand the invention in its various product/process/application aspects. These examples illustrate the preparation of polyamino acid particles which may or may not be loaded with active principles, and they also present the structural characteristics and properties of these particles.

EXAMPLES

Example 1

Preparation of the Poly(Sodium Glutamate)-Block-(Methyl Gluamate) Polymer

The techniques used for the polymerization of the NCAs to polymers having block or random structures are known to those skilled in the art and are given in detail in the book by H. R. KRICHELDORF "α-aminoacids-N-Carboxy Anhydrides and Related Heterocycles", Springer Verlag (1987). The following synthesis specifies the synthesis of one of them.

Synthesis of poly(GluOMe)$_{63}$-poly(GluOBz)$_{63}$: 10 g of NCA—GluOMe are solubilized in a mixture of 150 ml of dioxane and 450 ml of toluene at 60° C. 5 ml of a solution of 0.91 g of benzylamine in 50 ml of dioxane are added to the monomer in a single amount. After 1 h, 14.1 g of NCA-GluOBz, solubilized beforehand in a mixture of 20 ml of dioxane and 60 ml of toluene, are added. The polymerization continues for a further 19–24 h. The polymer is precipitated from the reaction medium in 2 liters of methanol, to which a further 500 ml of water are added. The solid obtained is filtered, and dried in an incubator at 50° C. under vacuum.

Yield: 90%. Composition by NMR 1 h (TFA-d) 45% molar GluOBz. Reduced viscosity (0.5% of TFA at 25° C.) 0.3 dl/g. Molar mass by GPC: 20,000 g/mol.

10 g of polymer are then reacted at 0° C. in 200 ml of TFA with 6 ml of trifluoromethanesulfonic acid for 15 min. During the hydrolysis of the benzyl groups, the polymer precipitates in the form of colloidal particles. After evaporation to dryness, the particles are taken up in water and neutralized at pH 7.4 with sodium hydroxide. A dialysis step ensures the elimination of the trifluoroacetate salts. The particles are finally isolated by lyophilization. Quantitative yield. Elemental analysis [Na] 8.2% (calculated composition 53% GluONa).

Example 2

Preparation of the Poly(Sodium Glutamate)-Block-(Ethyl Gluamate) Polymer

This polymer is prepared according to the method described in Example 1, using ethyl glutamate NCA and benzyl glutamate NCA in a 1:3 molar ratio. After the polymerization and debenzylation steps, the polymer is purified by dialysis at pH 7, and it is then lyophilized in order to obtain a white powder.

Example 3

Preparation of the Poly(Sodium Glutamate)-Block-(Hexadecyl Glutamate) Polymer This polymer is prepared according to the method described in Example 1, using dodecyl glutamate NCA and benzyl glutamate NCA in a 1:3 molar ratio. After the polymerization and debenzylation steps, the polymer is purified by dialysis at pH 7, and it is then lyophilized in order to obtain a white powder.

Example 4

Preparation of the Poly(Sodium Glutamate)-CO-(Dodecyl Glutamate) Polymer 10 g of polyglutamic acid (degree of polymerization 120) are dissolved in 200 ml of dimethyl sulfoxide. 15.5 g of $KHCO_3$ are then added, followed by 2.87 ml of iodododecane. The reaction medium is maintained at 60° C. for 40 hours under a nitrogen stream. The polymer is isolated by precipitation in 1.5 l of 0.1N hydrochloric acid, and the precipitate thus formed is washed several times in water. The desired colloidal suspension is obtained by adjusting the pH of the medium to 7.4 with sodium hydroxide, and is then dehydrated by lyophilization. The lyophilized polymer is finally washed several times in ethyl acetate, and dried under vacuum at 50° C. Composition by NMR (TFA-d): 12% of dodecylesterified glutamic acids. Residual water after lyophilization 10.5%. % elemental analysis (calc.): C 41.29 (42.15); H 5.99 (6.01); N 7.45 (7.63); Na 10.44 (10.45).

Example 5

Demonstration of the Nanoparticles by Light Scattering (LS) and by Transmission Electron Microscopy (TEM)

10 mg of particles of polymer 1 are suspended in 10 ml of water or in an aqueous salt solution. This solution is then introduced into a Coulter granulometer (or laser diffractometer). The results of the particle size analysis of the various products tested are given in Table 1 below.

TABLE 1

Measurements of DP size

| EXAMPLE | POLYMER | SIZE (nm) |
|---|---|---|
| Control | $POLY[(GLU-O-NA)_{1.0}]_k$ | NO PARTICLES (soluble product) |
| 1 | $POLY[(GLU-O-NA)_{0.63}\text{-BLOCK-}(GLU-O-METHYL)_{0.37}]_k$ | 100 |
| 2 | $POLY[(GLU-O-NA)_{0.66}\text{-BLOCK-}(GLU-O-ETHYL)_{0.34}]_k$ | 90 |
| 3 | $POLY[(GLU-O-NA)_{0.65}\text{-BLOCK-}(GLU-O-HEXADECYL)_{0.35}]_k$ | 110 |
| 4 | $POLY[(GLU-O-NA)_{0.88}\text{-CO-}(GLU-O-DODECYL)_{0.32}]_k$ | 15 |

Example 6

Test for Association of the Nanopaticles With a Protein (Insulin)

A solution of human insulin titrated at 1.4 mg/ml corresponding to 40 IU/ml is prepared using an isotonic phosphate buffer solution of pH 7.4. 10 mg of the DP prepared in Example 1 is dispersed in 1 ml of this insulin solution. After incubation for 15 hours at room temperature, the DP-associated insulin and the free insulin are separated by centrifugation (16,000 g, 1 hour) and ultrafiltration (filtration threshold 300,000 D). The free insulin recovered in the filtrate is assayed by HPLC or ELISA, and the amount of associated insulin is deduced therefrom by difference. The amount of DP-associated insulin is greater than 0.77 mg, which represents more than 55% of the total amount of insulin used.

The table below gives the results of the measurements of degree of association carried out on various DPs. The degree of association expresses the percentage of insulin associated, with respect to the insulin used, in a preparation titrated at 1.4 mg/ml of insulin and 10 mg/ml of DPs.

TABLE 2

Measurements of the degree of association with insulin for a 0.14 mg of insulin/mg of DP mixture

| EXAMPLE | POLYMER | DEGREE OF ASSOCIATION (%) |
|---|---|---|
| Controls | $POLY[GLU-O-NA]_{1.0}]_k$ | 0 |
| 1 | $POLY[(GLU-O-NA)_{0.60}\text{-BLOCK-}(GLU-O-METHYL)_{0.37}]_k$ | 55 |
| 2 | $POLY[(GLU-O-NA)_{0.66}\text{-BLOCK-}(GLU-O-ETHYL)_{0.34}]_k$ | 26 |
| 3 | $POLY[(GLU-O-NA)_{0.65}\text{-BLOCK-}(GLU-O-HEXADECYL)_{0.35}]_k$ | 36 |
| 4 | $POLY[(GLU-O-NA)_{0.88}\text{-BLOCK-}(GLU-O-DODECYL)_{0.12}]_k$ | >90 |

By way of comparison, insulin does not associate with sodium polyglutamate. This preliminary test is used to determine the optimum mixture of DP and of insulin in order to obtain an optimum formulation of DP and of insulin with a high degree of loading.

Example 7

Dissociation and Characterization of the Protein After Formulation Thereof With DPs (INSULIN) (INSULIN)

A formulation is prepared using DPs and insulin, the amounts of each being determined according to the degree of association measurements in Example 6.

A solution of human insulin titrated at 2.8 mg/ml corresponding to 80 IU/ml is prepared using an isotonic phosphate buffer solution of pH 7.4. 56 mg of the DP prepared in Example 1 are dispersed in 1 ml of this insulin solution. The pH and the isotonicity are adjusted, if necessary, in order to obtain a formulation at pH 7.4 and 280–300 mOs.

This preparation is diluted in increasing volumes of an isotonic 0.5% bovine albumin solution buffered at pH 7.4 with a 0.01 M phosphate buffer. The released insulin fraction is assayed by HPLC or ELISA. See attached figure. The released fraction increases with the dilution. All of the insulin is released on dilution 20. The assays by HPLC and ELISA show that >90% of the insulin is associated in this formulation.

Example 8

In-Vivo Test With DPs Loaded With a Therapeutic Protein (INSULIN)

A formulation is prepared using DPs and insulin, the amounts of each being determined according to the degree of association measurements in Example 6.

A group of 4 beagle dogs (males and females) weighing between 10 and 12 kg are fasted for 18 hours. A preparation is formulated according to Example 7 and consists of 80 IU of insulin and 56 mg of DPs (prepared according to Example 1) in 1 ml of PBS buffer. The dogs then receive a subcutaneous administration of this insulin preparation in a proportion of 1 IU/kg of weight. Blood is sampled for a glucose assay and an insulin assay before (−2 h, −1 h and 0 h) and after (1 h, 2 h, 4 h, 6 h, 12 h, 16 h, 20 h, 24 h, 28 h, 32 h, 36 h, 40 h, 44 h, 48 h) injection. The glucose concentrations are measured in the samples using the glucose oxidase method, and the serum insulin is 25 assayed using a radio-immunological method.

BRIEF DESCRIPTION OF THE DRAWINGS

The attached FIG. 1 follows the mean of the evolution, as a function of the time T in hours (h), of the serum insulin and glucose for the DPs prepared according to Example 1. The -•- curve is that of the insulinemia expressed in international milliunits.

The -o- curve is that of the glycemia expressed in mmol/l.

Figure 1:
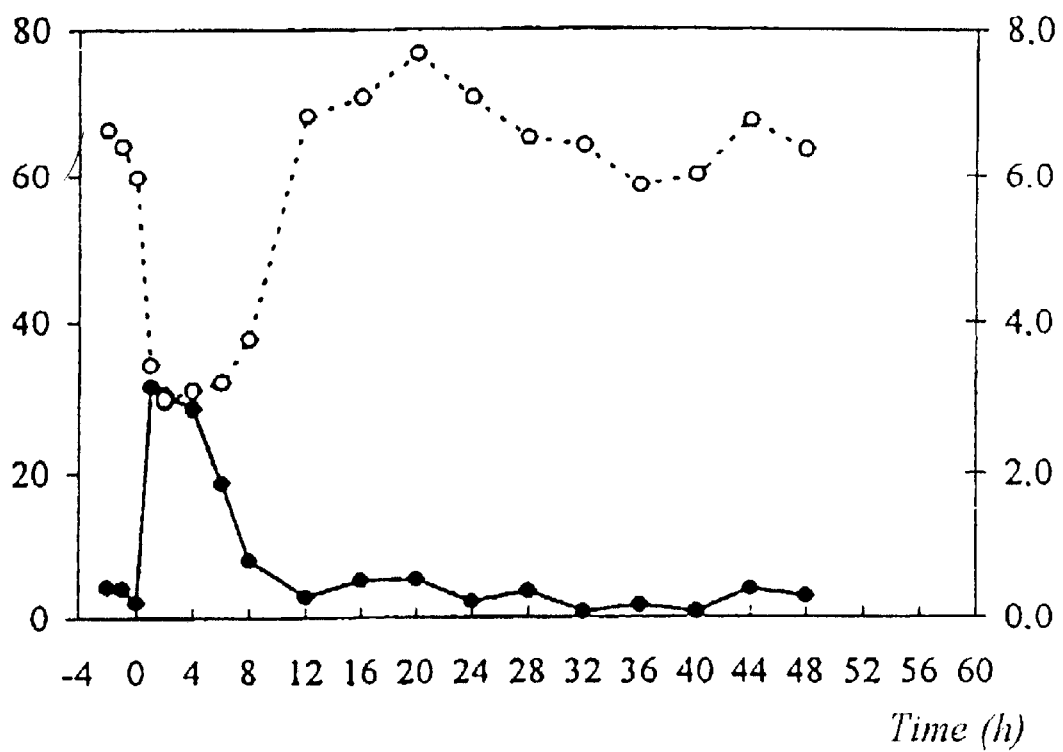

Table 3 below shows the results of the duration of action of insulin in the presence of the various DPs according to Examples 1 to 5.

TABLE 3

Measurements of the time of action of the insulin (hypoglycemia-producing effect) in the presence of DPs according to the invention

| EXAMPLE | POLYMER | TIME FOR RETURN TO BASAL LEVEL (h) |
|---|---|---|
|  | SOLUBLE INSULIN (WITHOUT DPs) | 1 |
|  | POLY[(GLU-O-NA)$_{1.0}$]$_k$ | 1 |
| 1 | POLY[(GLU-O-NA)$_{0.63}$-BLOCK-(GLU-O-METHYL)$_{0.037}$]$_k$ | 12 |
| 2 | POLY[(GLU-O-NA)$_{0.66}$-BLOCK-(GLU-O-ETHYL)$_{0.34}$]$_k$ | 15 |
| 3 | POLY[(GLU-O-NA)$_{0.65}$-BLOCK-(GLU-O-HEXADECYL)$_{0.35}$]$_k$ | 20 |
| 4 | POLY (GLU-O-NA)$_{0.88}$-CO-(GLU-O-DODECYL)$_{0.12}$]$_k$ | 12 |

This example demonstrates the nondenaturation of the insulin in the presence of DPs according to the invention.

In addition, this Example 8 makes it possible to demonstrate the increase in the duration of action of the insulin and, therefore, the usefulness of the DPs as a delay system for the controlled release of insulin. It also shows how the duration of action can be controlled through the judicious choice of the hydrophobic group.

What is claimed is:

1. A composition comprising particles of amphiphilic, linear polyaminoacids (PAAs) having α-peptide chains of recurrent aminoacids (rAAs), wherein:
    said particles having a mean particle size of less than 200 μm;
    said particles being spontaneously obtainable by bringing the PAAs into contact with an aqueous liquid medium, in which the hydrophilic portion of the PAAs solubilizes more than the hydrophobic portion of said PAAs, such that the latter precipitate while becoming organized in discrete supramolecular arrangements and so forming spontaneously colloidal suspensions of particles compatible with the pH of physiological media;
    said particles being capable of spontaneous association with at least one active principle (AP) in an aqueous medium;
    said particles associated with at least one AP being capable of releasing the AP in vivo, under physiological conditions, in a sustained and controlled way;
    all the rAAs being selected from the group consisting of aspartates and glutamates;
    said rAAs being identical to or different from one to another; some of said rAAs bearing at least one hydrophobic $R^0$ group which, when more than one $R^0$ group is present on the rAA, may be identical or different.

2. A composition according to claim 1, wherein said particles have a mean particle size of less than 100 μm.

3. A composition according to claim 1, wherein said particles have a mean particle size of from 0.01 to 20 μm.

4. A composition according to claim 1, wherein said particles have a mean particle size of from 0.01 to 0.5 μm.

5. A composition according to claim 1, wherein $R^0$ is distributed on the polymer chains in a random or ordered manner.

6. A composition according to claim 1, wherein $R^0$ is selected from the group consisting of
    (i) a linear or branched member selected from the group consisting of alkyl, acyl and alkenyl;
    (ii) a hydrocarbon-based group containing one or more heteroatoms;
    (iii) a member selected from the group consisting of aryl, aralkyl and alkylaryl;
    (iv) a natural hydrophobic derivative.

7. A composition according to claim 1, wherein $R^0$ is selected from the group consisting of
    (i) a member selected from the group consisting of a linear $C_1$–$C_{20}$ alkyl, a linear $C_1$–$C_{20}$ acyl and a linear $C_1$–$C_{20}$ alkenyl;
    (ii) a hydrocarbon-based group containing one or more heteroatoms selected from the group consisting of oxygen and sulfur;
    (iii) aryl; and
    (iv) a member selected from the group consisting of cholesterol, phosphatidylcholines and diacylglycerols.

8. A composition according to claim 1, wherein $R^0$ is selected from the group consisting of
    (i) a member selected from the group consisting of a linear $C_2$–$C_{18}$ alkyl, a linear $C_2$–$C_{18}$ acyl and a linear $C_2$–$C_{18}$ alkenyl;
    (ii) a hydrocarbon-based group containing oxygen and/or sulfur and having the following formula:

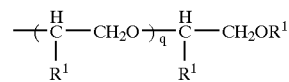

wherein the $R^1$ radicals are identical to or different from one another, and correspond to hydrogen or to a radical in (i) above; and q=1 to 100;
    (iii) aryl; and
    (iv) a member selected from the group consisting of cholesterol, phosphatidylcholines and diacylglycerols.

9. A composition according to claim 1, wherein the $R^0$ group is selected from the group consisting of methyl, ethyl, propyl, hexyl, octyl, dodecyl, hexadecyl and octadecyl.

10. A composition according to claim 1, wherein the hydrophobic $R^0$ group is linked to the rAA chain by a covalent bond.

11. A composition according to claim 10, wherein the covalent bond can be cleaved by chemical, and/or enzymatic hydrolysis.

12. A composition according to claim 10, wherein the covalent bond is an ester or amide bond.

13. A composition according to claim 1, wherein the proportion of hydrophobic rAAs present in said composition is greater than or equal to 3%.

14. A composition according to claim 1, wherein the proportion of hydrophobic rAAs present in said composition is from 3 to 70%.

15. A composition according to claim 1, wherein the proportion of, hydrophobic rAAS present in said composition is from 3 to 60%.

16. A composition according to claim 1, wherein the PAAs comprise up to approximately 1000 rAAS.

17. A composition according to claim 1, wherein the PAAs comprise up to approximately 500 rAAs.

18. A composition according to claim 1 wherein said particles are aggregated.

19. A pharmaceutical composition comprising the composition of claim 1 associated with a pharmaceutically active ingredient in an amount sufficient to extend the availability of the pharmaceutically active ingredient in the circulation of a patient in a controlled and sustained manner.

20. A colloidal suspension of the composition according to claim 1.

21. An aqueous colloidal suspension of the composition according to claim 1.

22. A process for preparing the colloidal suspension according to claim 20,
   I—in using linear PAAs containing α-peptide chains of recurrent amino acids (rAAs) selected from natural polar amino acids, namely glutamic acid and aspartic acid, and/or from the salts thereof, respectively glutamates and aspartates; some of these rAAs each bearing at least one hydrophobic $R^o$ group, these $R^o$ groups being identical to or different from one another;
   II—in placing the amphiphilic PAAs in an aqueous medium;
   III—and then in making at least the rAAs carrying $R^o$ insoluble without the medium, so as to to form discrete supramolecular arrangements.

23. A process according to claim 22, wherein a pharmaceutically active compound is present in the aqueous medium such that the colloidal particles produced comprise particles loaded with the active compound.

24. A process according to claim 22 further comprising aggregating said particles.

25. A process according to claim 24 wherein said particles are aggregated using an aggregation agent selected from the group consisting of a salt, an acid, a base, a polymer and mixtures thereof.

26. A process according to claim 25, wherein the polymer is an ionic polymer.

27. A pharmaceutical composition according to claim 19, wherein the active ingredient is selected from the group consisting of
   a) proteins and/or polypeptides;
   b) polysaccharides;
   c) nucleic acids; and
   d) mixtures of a), b) and c).

28. A pharmaceutical composition comprising:
   a precursor of the composition according to claim 1, said precursor comprising an amphiphilic, linear polyaminoacid (PAA) having α-peptide chains of recurrent amino-acids (rAAs);
      said rAAs being identical to or different from one another;
      said rAAs being selected from the group consisting of the natural Polar amino acids Glu and Asp and salts thereof;
      wherein some of the rAAs bear at least one hydrophobic $R^o$ group which, when more than one $R^o$ group is present on the rAA, may be identical or different,
   and an active ingredient is selected from the group consisting of
   a) proteins and/or polypeptides;
   b) polysaccharides;
   c) nucleic acids; and
   d) mixtures of a), b) and c).

29. A composition comprising the suspension according to claim 20, and an active ingredient selected from the group consisting of
   a) proteins and/or polypeptides;
   b) polysaccharides;
   c) nucleic acids; and
   d) mixtures of a), b) and c).

30. A pharmaceutical composition according to 19, wherein the active ingredient is selected from the group consisting of
   a) hemoglobins, cytochromes, albumins, interferons, antigens, antibodies, erythropoietin, insulin, growth hormones, factor IX, interleukins and mixtures thereof;
   b) heparin;
   c) a nucleic acid selected from the group consisting of oligosaccharides of RNA, DNA and mixtures thereof; and
   d) mixtures of a), b) and c).

31. A composition comprising the precursor according to claim 28 and an active ingredient selected from the group consisting of
   a) hemoglobins, cytochromes, albumins, interferons, antigens, antibodies, erythropoietin, insulin, growth hormones, factor IX, interleukins and mixtures thereof;
   b) heparin;
   c) a nucleic acid selected from the group consisting of oligosaccharides of RNA, DNA and mixtures thereof; and
   d) mixtures of a), b) and c).

32. A composition comprising the suspension according to claim 20 and an active ingredient selected from the group consisting of
   a) hemoglobins, cytochromes, albumins, interferons, antigens, antibodies, erythropoietin, insulin, growth hormones, factor IX, interleukins and mixtures thereof;
   b) heparin;
   c) a nucleic acid selected from the group consisting of oligosaccharides of RNA, DNA and mixtures thereof; and
   d) mixtures of a), b) and c).

33. A pharmaceutical composition according to claim 19, wherein the active ingredient is a vaccine.

34. A composition according to claim 20, wherein the active ingredient is a vaccine.

35. A composition according to claim 28, wherein the active ingredient is a vaccine.

36. A composition comprising the composition of claim 1 and a member selected from the group consisting of a nutritional product, a cosmetic product and a plant protection agent.

37. A composition according to claim 31, wherein the active ingredient is selected from the group consisting of a nutritional product, a cosmetic product and a plant protection agent.

38. A composition according to claim 32, wherein the active ingredient is selected from the group consisting of a nutritional product, a cosmetic product and a plant protection agent.

39. A method of treating diabetes, comprising administering to a patient an effective amount of the pharmaceutical composition according to claim 19.

40. A composition according to claim 1, wherein said particles have a mean particle size of from 0.01 to 0.2 µm.

* * * * *